US012685671B2

(12) United States Patent
Vankov et al.

(10) Patent No.: US 12,685,671 B2
(45) Date of Patent: Jul. 21, 2026

(54) CALIBRATION PROCESS FOR FEMTOSECOND LASER INTRAOCULAR LENS MODIFICATION SYSTEM USING VIDEO AND OCT TARGETING

(71) Applicant: AMO Development, LLC, Irvine, CA (US)

(72) Inventors: Alexander Vankov, Mountain View, CA (US); Jenny Wang, Mountain View, CA (US); David A. Dewey, Sunnyvale, CA (US); Phillip Gooding, Mountain View, CA (US); Richard Hofer, Santa Cruz, CA (US); Georg Schuele, Portola Valley, CA (US)

(73) Assignee: AMO DEVELOPMENT, LLC, Irvine, CA (US)

( * ) Notice: Subject to any disclaimer, the term of this patent is extended or adjusted under 35 U.S.C. 154(b) by 190 days.

(21) Appl. No.: 18/772,786

(22) Filed: Jul. 15, 2024

(65) Prior Publication Data

US 2025/0009558 A1     Jan. 9, 2025

Related U.S. Application Data

(62) Division of application No. 17/057,691, filed as application No. PCT/IB2020/053354 on Apr. 8, 2020, now Pat. No. 12,042,434.

(Continued)

(51) Int. Cl.
*A61F 9/008* (2006.01)
*G02B 26/10* (2006.01)

(52) U.S. Cl.
CPC ........ *A61F 9/00834* (2013.01); *G02B 26/101* (2013.01); *A61F 2009/00855* (2013.01);
(Continued)

(58) Field of Classification Search
CPC ........ A61F 9/00834; A61F 2009/00855; A61F 2009/0087; A61F 2009/00897; A61F 2009/00851; A61F 2/16; G02B 26/101
See application file for complete search history.

(56) References Cited

U.S. PATENT DOCUMENTS

| | | | |
|---|---|---|---|
| 4,590,598 A * | 5/1986 | O'Harra, II | ............. A61F 9/008 372/32 |
| 8,845,625 B2 | 9/2014 | Angeley et al. | |

(Continued)

FOREIGN PATENT DOCUMENTS

WO      2015148462 A1    10/2015

*Primary Examiner* — Scott M. Getzow

(57) ABSTRACT

The XYZ beam position of an ophthalmic laser system is calibrated by measuring a fluorescent signal induced by the focused laser beam in a thin glass coverslip via multiphoton absorption. A video camera measures the XY position and intensity of the fluorescent signal as the focused laser beam strikes the coverslip. The Z position of the focus is determined by scanning the targeted z position and identifying the Z scanner position of peak fluorescence. An OCT system measures the real space Z location of the coverslip, which is correlated with the Z scanner position. Other laser system parameters are assessed by repeatedly scanning a lower energy laser beam in a piece of IOL material, and observing damage (scattering voids) formation in the IOL material. Based on the rate of damage formation, laser system parameters such as beam quality, numerical aperture, pulse energy, and pulse duration, etc. can be assessed.

3 Claims, 5 Drawing Sheets

S31: Repeatedly scan low energy laser beam in IOL material piece in a scan pattern S32: Observe formation of scattering voids (damage) in IOL material after repeats of laser scans, using video camera and/or OCT; determine rate of damage formation (e.g. number of repeated scans required)

S33: Assess effective laser intensity (a function of beam quality, numerical aperture, laser energy, pulse duration, etc.) based on observed rate of damage formation

Related U.S. Application Data

(60) Provisional application No. 62/906,611, filed on Sep. 26, 2019, provisional application No. 62/832,842, filed on Apr. 11, 2019.

(52) U.S. Cl.
CPC ................. *A61F 2009/0087* (2013.01); *A61F 2009/00897* (2013.01)

(56) References Cited

U.S. PATENT DOCUMENTS

| | | | |
|---|---|---|---|
| 9,603,743 | B2 | 3/2017 | Rathjen et al. |
| 9,918,873 | B2 | 3/2018 | Woodley et al. |
| 10,105,261 | B2 | 10/2018 | Simoneau et al. |
| 2007/0173797 | A1 | 7/2007 | Zickler |
| 2009/0224174 | A1 | 9/2009 | Netz et al. |
| 2010/0324543 | A1 | 12/2010 | Kurtz et al. |
| 2013/0188035 | A1 | 7/2013 | Goodwin |
| 2015/0282988 | A1 | 10/2015 | Simoneau et al. |
| 2019/0053947 | A1 | 2/2019 | Simoneau et al. |
| 2019/0209376 | A1 | 7/2019 | Neev |
| 2019/0307554 | A1 | 10/2019 | Schuele et al. |
| 2020/0038241 | A1* | 2/2020 | Wang ................. A61F 9/00814 |
| 2022/0015949 | A1 | 1/2022 | Vankov et al. |

* cited by examiner

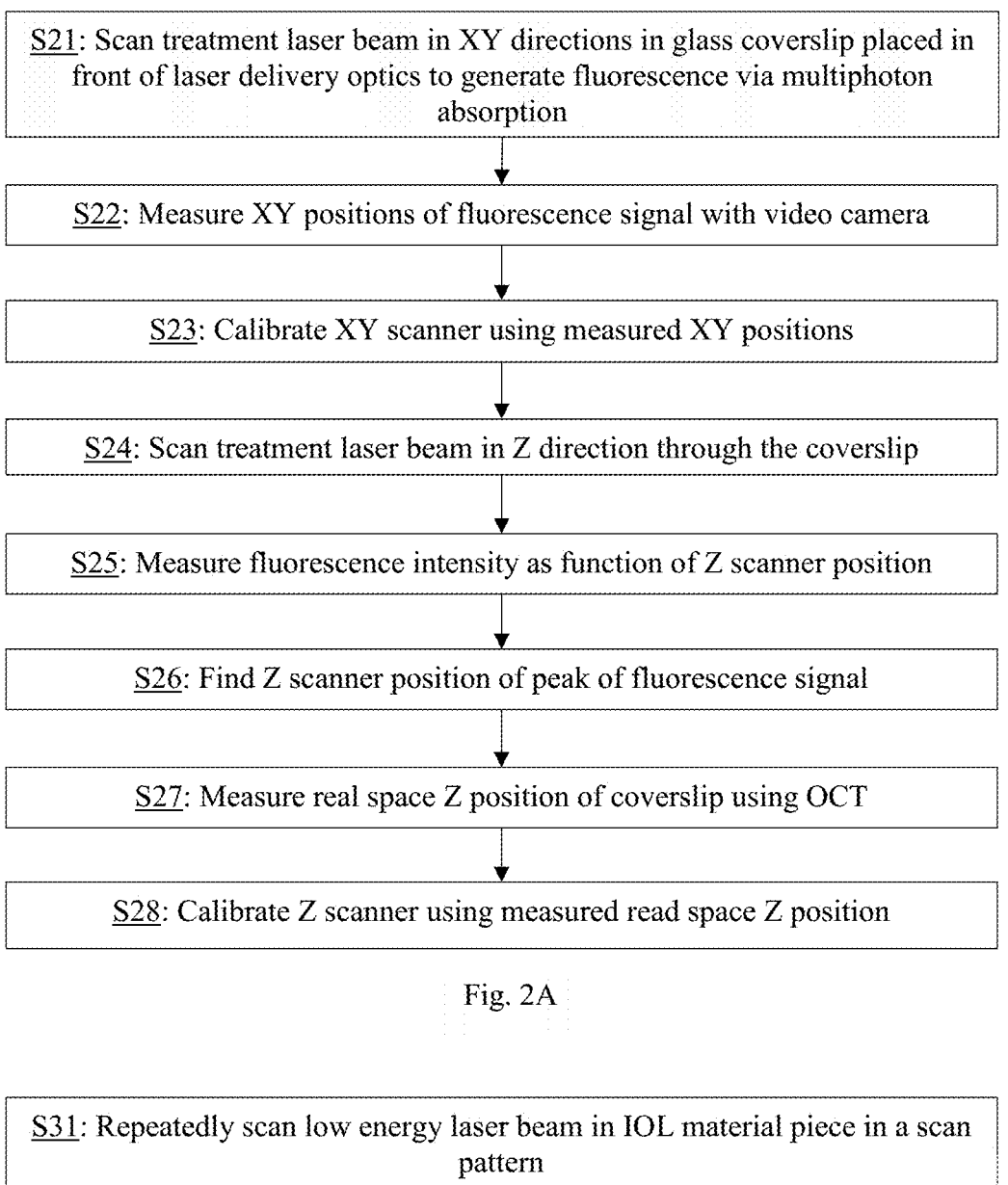

S21: Scan treatment laser beam in XY directions in glass coverslip placed in front of laser delivery optics to generate fluorescence via multiphoton absorption S22: Measure XY positions of fluorescence signal with video camera S23: Calibrate XY scanner using measured XY positions S24: Scan treatment laser beam in Z direction through the coverslip S25: Measure fluorescence intensity as function of Z scanner position S26: Find Z scanner position of peak of fluorescence signal S27: Measure real space Z position of coverslip using OCT S28: Calibrate Z scanner using measured read space Z position

Fig. 2A

S31: Repeatedly scan low energy laser beam in IOL material piece in a scan pattern S32: Observe formation of scattering voids (damage) in IOL material after repeats of laser scans, using video camera and/or OCT; determine rate of damage formation (e.g. number of repeated scans required)

S33: Assess effective laser intensity (a function of beam quality, numerical aperture, laser energy, pulse duration, etc.) based on observed rate of damage formation

Fig. 2B

CALIBRATION PROCESS FOR FEMTOSECOND LASER INTRAOCULAR LENS MODIFICATION SYSTEM USING VIDEO AND OCT TARGETING

CROSS-REFERENCES TO RELATED APPLICATIONS

This application is a divisional application based on U.S. patent application Ser. No. 17/057,691, filed Nov. 23, 2020, which is a U.S. national stage of and claims the benefit under 35 U.S.C. § 371 of International Patent Application No. PCT/IB2020/053354, filed Apr. 8, 2020, which claims priority of U.S. Provisional Application Nos. 62/906,611, filed Sep. 26, 2019 and 62/832,842, filed Apr. 11, 2019, all of which are incorporated herein by reference in their entirety.

BACKGROUND OF THE INVENTION

Field of the Invention

This invention relates to calibration of an ophthalmic laser system, and in particular, it relates to a calibration method for a laser system used for IOL (intraocular lens) modification.

Description of Related Art

Despite decades of optimization of pre-operative diagnostics and lens calculation formulas, approximately 30% of cataract surgery patients are left with visually significant refractive error (>0.5D). To correct this and other aberrations, a femtosecond laser system can be used to modify the properties of the intraocular lens while it is in the eye. If modified in the proper way, the lens can correct any refractive errors in the eye. To achieve the necessary precision for successful correction, the laser system must be properly calibrated to modify the intraocular lens material in the exact desired 3D volume and to the intended degree.

There are currently several techniques used to identify the XYZ position of femtosecond laser focus which is intended to be scanned across a 3D liquid-like volume. For example, the effects of laser-induced breakdown in a liquid or solid material can be observed using visual or auditory feedback as the laser beam focus is moved throughout the volume. By placing and moving an interface in a known way, the Z position of the focus can also be determined. However, this requires a laser beam with enough energy to induce breakdown and the plasma formation from breakdown could produce bubbles which impede subsequent measurements or destroy the test material. A fluorescent plate can also be used to identify the XYZ position in a nondestructive way but requires a special material.

To characterize the beam quality and laser energy, an external, high magnification beam camera can be placed to image the focused beam and a power meter can be used to measure the laser energy. However, these require external equipment which are difficult to use rapidly across the whole scan field especially in a liquid environment.

SUMMARY

The present invention is directed to a laser system calibration method that substantially obviates one or more of the problems due to limitations and disadvantages of the related art.

An object of the present invention is to provide a laser system calibration method that is inexpensive and automatic, and that can provide rapid assessment of system status in a treatment-like setting.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a method for calibrating and operating an ophthalmic laser system, which includes: generating a pulsed laser beam; controlling a position of an XY scanner of the ophthalmic laser system to scan the laser beam in XY directions in a glass coverslip placed in front of laser delivery optics of the ophthalmic laser system to generate fluorescence signals in the coverslip via multiphoton absorption; controlling an imaging subsystem (e.g. a video camera) of the ophthalmic laser system to measure XY positions of the fluorescence signals; calibrating the XY scanner by correlating the XY positions of the fluorescence signals measured by the video camera to the position of the XY scanner; controlling a position of a Z scanner of the ophthalmic laser system to scan the laser beam in a Z direction through the coverslip; controlling the imaging subsystem (e.g. the video camera) to measure a fluorescence signal intensity as a function of a Z scanner position; finding a Z scanner position that corresponds to a peak of the measured fluorescence signal intensity; controlling the imaging subsystem (e.g., an OCT (optical coherence tomography) device) to measure a real space Z position of the coverslip; and calibrating the Z scanner by correlating the measured real space Z position and the Z scanner position that corresponds to the peak of the measured fluorescence signal intensity.

In another aspect, the present invention provides a method for calibrating and operating an ophthalmic laser system, which includes: generating a low energy pulsed laser beam, the low energy laser beam having a pulse energy configured to cause formation of damages in an IOL (intraocular lens) material only after multiple irradiations; controlling a laser delivery optical subsystem of the ophthalmic laser system to repeatedly scan the low energy laser beam in a piece of IOL material; controlling an imaging subsystem (e.g. video camera or OCT device) of the ophthalmic laser system to measure formation of damages in the piece of IOL material after repeats of laser scans, and to determine a rate of damage formation; and determining an effective laser intensity of the laser beam based on the rate of damage formation.

It is to be understood that both the foregoing general description and the following detailed description are exemplary and explanatory and are intended to provide further explanation of the invention as claimed.

BRIEF DESCRIPTION OF THE DRAWINGS

FIGS. 2A and 2B schematically illustrate a laser system calibration method according to embodiments of the present invention.

DETAILED DESCRIPTION OF PREFERRED EMBODIMENTS

Commonly owned, co-pending U.S. patent application Ser. No. 16/375,784, filed Apr. 4, 2019, entitled Methods and Systems for Changing a Refractive Property of an Implantable Intraocular Lens ("the '784 application"), describes a "method of altering a refractive property of a crosslinked acrylic polymer material by irradiating the material with a high energy pulsed laser beam to change its refractive index. The method is used to alter the refractive property, and hence the optical power, of an implantable intraocular lens after implantation in the patient's eye. In some examples, the wavelength of the laser beam is in the far red and near IR range and the light is absorbed by the crosslinked acrylic polymer via two-photon absorption at high laser pulse energy. . . . The method can be used to form a Fresnel lens in the optical zone [of the IOL]."(Abstract.) As described in the '784 application, the IOL may be formed of a crosslinked acrylic polymer, and the refractive index modification is achieved through heating of the material. The laser beam may be in the blue range, or the red and near infrared range, in which case the IOL material absorbs the laser light through two-photon absorption. The content of the '784 application is incorporated herein by reference in its entirety.

Figure 1:
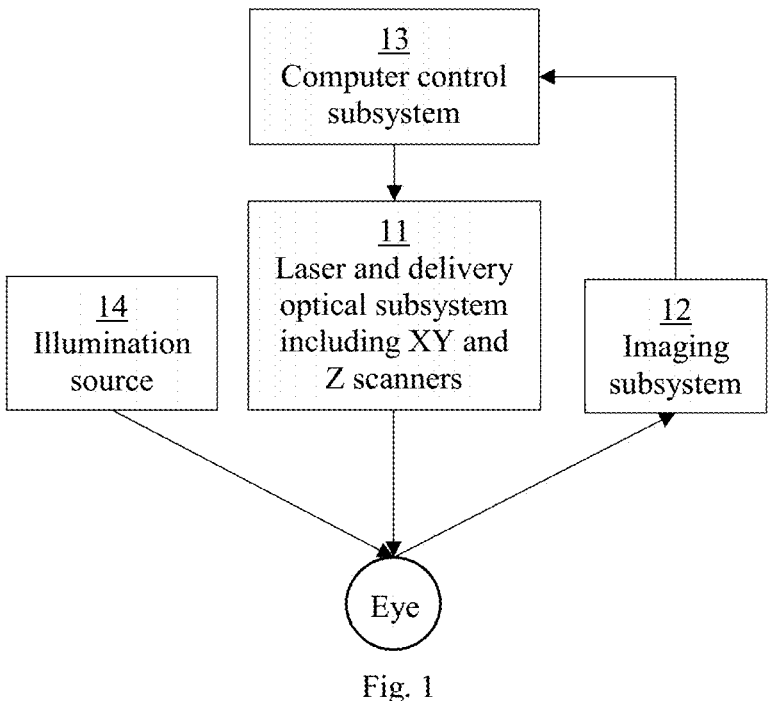
FIG. 1 schematically illustrates an ophthalmic laser surgical system in which embodiments of the present invention may be implemented.

FIG. 1 schematically illustrates an ophthalmic laser surgical system in which embodiments of the present invention may be implemented. The system includes a laser device and associated beam delivery optical subsystem 11 for delivering a pulsed laser beam to the eye for treatment, an imaging subsystem 12 for detecting a signal from the eye, and a computer control subsystem 13 that performs control and data processing functions. The beam delivery optical subsystem 11 includes XY and Z scanners to scan the laser beam focus in three dimensions. For example, the XY scanner may be implemented by two rotating mirrors, and the Z scanner may be implemented by a lens actuator that moves a lens along the optical axis (Z direction). In some embodiments, the ophthalmic laser surgical system also includes an external illumination source 14. The imaging subsystem 12 may be implemented by different devices in the different embodiments described below, including, for example, a video imaging system and/or an OCT system. Although not shown in FIG. 1, the imaging subsystem 12 and the beam delivery optical subsystem 11 may share certain optical components in some embodiments. Many types of ophthalmic laser surgical system are known in the art and their detailed descriptions are omitted here. For example, commonly owned U.S. Pat. No. 8,845,625, which is incorporated herein by reference in its entirely, discloses in its FIGS. 1-4 and accompanying descriptions in the specification, an ophthalmic laser surgical system that includes an ultrafast laser source, a beam delivery optical subsystem including scanning devices, an OCT (optical coherence tomography) subsystem, an imaging subsystem such as a video monitoring subsystem for viewing an image of the eye, an aim beam subsystem, and related control subsystem.

In IOL refractive index modification, proper calibration of the laser system is important. Identification of the femtosecond laser focus must be done rapidly across the potential target volume and registered to the imaging subsystem (e.g., targeting video and/or OCT system). An automatic, non-destructive technique is important for covering the large volume in a reasonable amount of time. Due to the nonlinear multiphoton processes that drive the material modification when using focused femtosecond laser pulses, accurate assessment of the effective laser intensity in the focus, a function of beam quality, numerical aperture, and laser energy, is also important. A rapid technique to estimate the effective laser intensity is also crucial to calibration of the system.

Embodiments of the present invention provide a calibration process for femtosecond laser IOL modification system which uses video and OCT targeting. The process has two parts.

Referring to FIG. 2A, the first part of the calibration process assesses XYZ position targeting of the laser system by placing a thin glass coverslip in front of an objective lens of the laser beam delivery optics, and measuring a fluorescent signal induced by the focused laser beam in the coverslip. Here, the Z direction is the direction of the optical axis of the laser beam delivery optics, and X and Y directions are perpendicular to the Z direction. The laser beam is scanned in XY directions in glass coverslip, by moving the positions of the XY scanner (step S21). A video camera (a part of the imaging subsystem 12) is used to visualize and measure the XY position and intensity of the fluorescent signal as the focused laser beam strikes the coverslip (step S22). The XY position as measured by the video camera is correlated to the XY scanner position that delivered the corresponding laser pulses (step S23). This accomplishes the calibration of the XY scanner. The Z position of the focus is determined by scanning the targeted Z position (step S24) using the Z scanner of the laser beam delivery subsystem, measuring the fluorescence intensity as a function of the Z scanner position (step S25), and identifying the Z scanner position that corresponds to peak fluorescence (step S26). The targeting OCT (a part of the imaging subsystem 12) is used to measure the real space Z location of the coverslip (step S27), and a correlation between the Z scanner position and the real space Z location is established (step S28), which accomplishes Z scanner calibration.

In this method, the fluorescence is induced in the glass by the femtosecond laser beam via a multiphoton (e.g. two-photon) absorption process, which allows for precise z location targeting. The signal is strong even at laser energies beneath the glass breakdown thresholds, which makes this a nondestructive technique without the need for any special fluorescent material. Moreover, the glass coverslip can be easily submergible in any kind of liquid volume to most closely simulate the system use case.

Referring to FIG. 2B, the second part of the calibration process uses a blank disc of IOL material to assess effective laser intensity by firing the laser beam into the material until scattering voids (damage) form due to multiphoton absorption. Low laser energy is used to scan in the IOL material (step S31), so that multiple irradiations are required to form voids in the IOL material. In other words, the low energy laser beam is configured to cause void formation in the IOL only after multiple irradiations. The voids can be observed by the video camera and/or by the OCT system, and the rate of void formation (e.g. the number of repeated scans required before voids start to form) is determined through this observation (step S32). The rate of void formation may be used to determine the effective laser intensity of the system (step S33). For example, the rate of void formation is sensitive to change in beam quality (e.g. the $M^2$ value (beam propagation ratio), which determines how small the beam waist can be focused), numerical aperture, laser energy, and pulse duration, and gives a rapid assessment of the effective laser intensity in the most relevant environment. This process is destructive and should be done on a fresh target each time.

Thereafter, the effective laser intensity determined in this calibration process may be used to design the laser treatment plan, for example, to select parameters such the laser pulse energy, the number of laser pulses or scan passes required to achieve a predetermined amount of refractive index change in the IOL material, etc.

The process of assessing XYZ position targeting of the laser system (FIG. 2A) and the process of assessing the effective laser intensity (FIG. 2B) may be practiced independently of each other, and provide assessments of two different aspects of the laser and optical delivery subsystem 11. In combination, these two parts of the calibration process allow for inexpensive, automatic calibration of the XYZ targeting and rapid assessment of system status in a treatment-like setting prior to using the system for IOL modification and correction.

The calibration process may be automated using the control subsystem 13, which automatically controls the movements of the laser and delivery optical subsystem 11 and the acquisition of image data by the imaging subsystem 12, as well as the processing of image data, according to the procedures described above. After calibration, the laser system may be operated to treat a patient, e.g. to modify the refractive index of an IOL in the patient's eye by scanning a laser beam in the patient's eye.

Figure 3:
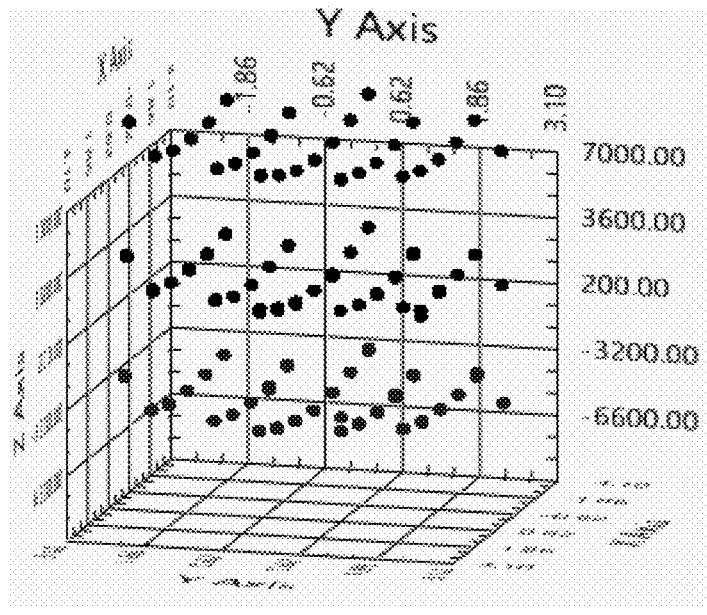
FIG. 3 shows measured XYZ positions of the fluorescence signal in a coverslip illuminated by a laser beam according to an embodiment of the present invention.

In one example, a thin glass coverslip approximately 150 μm thick is immersed in a beaker of water. This beaker is placed on a motorized stage which moves the coverslip to three different Z levels which span the targeted volume. FIG. 3 shows measured XYZ positions of the fluorescence signal with the coverslip at three different levels of the motorized stage.

Figure 4A:
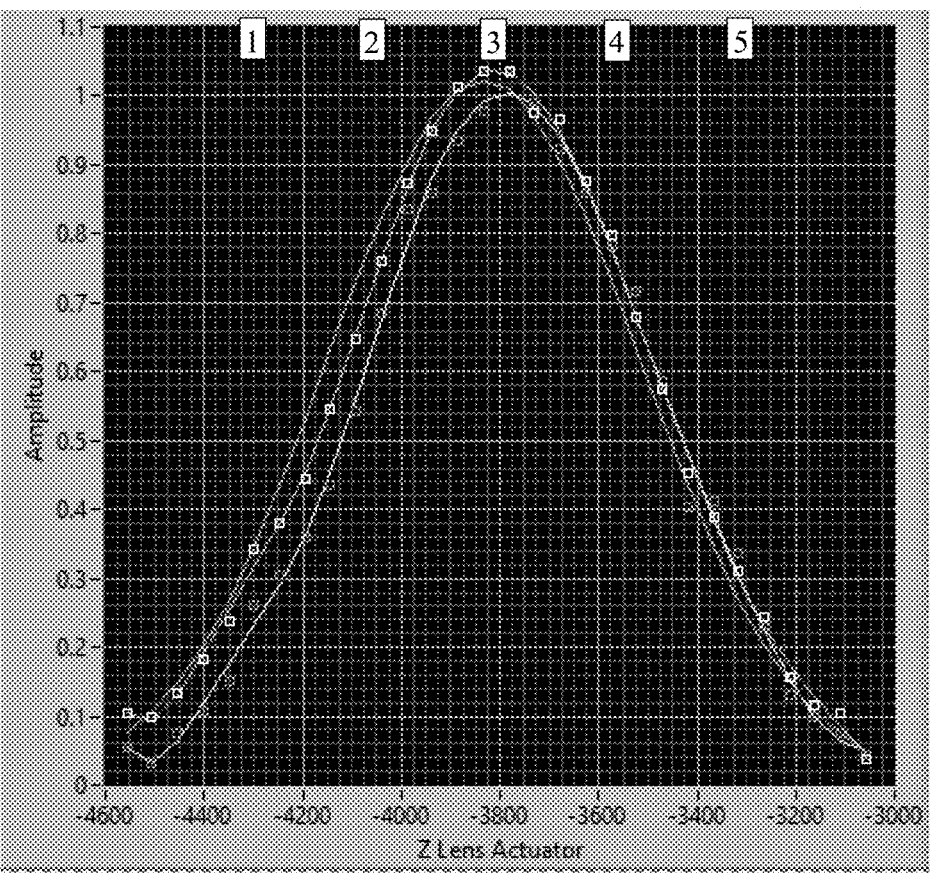
FIG. 4A shows curves of the measured fluorescence intensity vs. the Z scanner position used for Z position calibration according to an embodiment of the present invention.
Figure 4B:
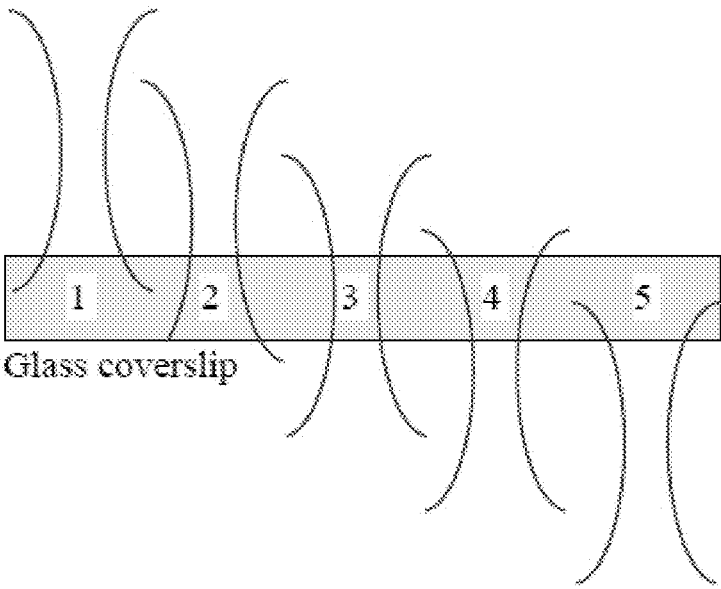
FIG. 4B schematically illustrates the shape and locations of the beam focus relative to the glass coverslip at the five Z locations indicated in FIG. 4A.

More specifically, the laser beam focus is moved by the XY scanners to given XY positions, which are determined by the position of the fluorescent spot in the image taken by the video camera (a part of the imaging subsystem 12). The video camera has a notch filter which prevents the laser wavelength light from illuminating the camera, so only the fluorescent signal and not the original laser beam is measured by the video camera. This calibrates the XY scanners to the real space as defined by the video camera. The fluorescence intensity generated by the laser beam focus is measured from the video camera image by summing the intensity in the pixels surrounding the target position. The Z scanner scans the laser beam focus in the Z direction, through the targeted Z position, and the fluorescence intensity corresponding to each Z scanner position is measured. The peak of the fluorescence intensity occurs when the laser beam focus is in the middle of the glass coverslip. FIG. 4A shows three curves of the measured fluorescence intensity vs. the Z scanner position, from which the peak Z position can be determined. FIG. 4B schematically illustrates the shape and locations of the beam focus relative to the glass coverslip at the five Z locations labeled 1 to 5 in FIG. 4A. As seen in FIG. 4B, due to the relative sizes of the beam focus and the coverslip thickness, the fluorescence is the strongest when the beam focus is located near the center depth of the coverslip. The glass coverslip position in real space is determined by the OCT image of the glass coverslip. This calibrates the Z scanner to place the laser focus at the desired Z location as defined by the OCT.

The measurement steps are repeated rapidly at multiple target locations over a potential treatment area (e.g. 6 mm squared) and for a number of (e.g. three) different Z levels. A computer with appropriate control software (e.g., a LabView routine) may be used to command the XYZ scanners, select the proper video pixels for analysis, set the laser intensity, fit the fluorescence intensity curve and determine the peak, and to determine the Z position of the coverslip using OCT. Using the multiple target locations, the deviation from the expected XYZ actuator positions are calculated and a correction can be implemented.

Figure 5:
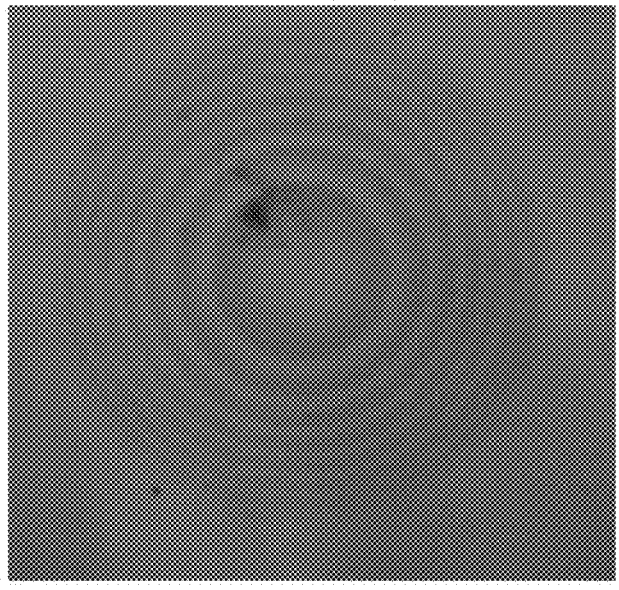
FIG. 5 shows low energy ring patterns used for assessing targeting and effective laser intensity according to an embodiment of the present invention.

In another example, a flat button of IOL material (an IOL itself may also be used) is placed into a beaker and moved to the expected laser beam target location. Then, the laser beam is scanned in the IOL material in a ring pattern (see FIG. 5) which mimics a pattern used in the IOL refractive index modification. The laser scanning process is done at a sufficiently low laser energy that it requires multiple repeats of the pattern before damage is created in the form of voids formation. This damage is visible in the OCT image as highly scattering dots. Observations of the damage formation may be made manually based on the OCT images, and positions of the dots may be measured using image processing techniques. These measured positions of the dots are matched to the targeted XYZ location to perform a second validation of the XYZ position targeting. The number of repeated laser scanning patterns required before damage starts to occur is sensitive to the effective laser intensity (which is a function of beam quality, numerical aperture, laser energy, and pulse duration) and serves as a valuable rapid check of system performance.

Figure 6:
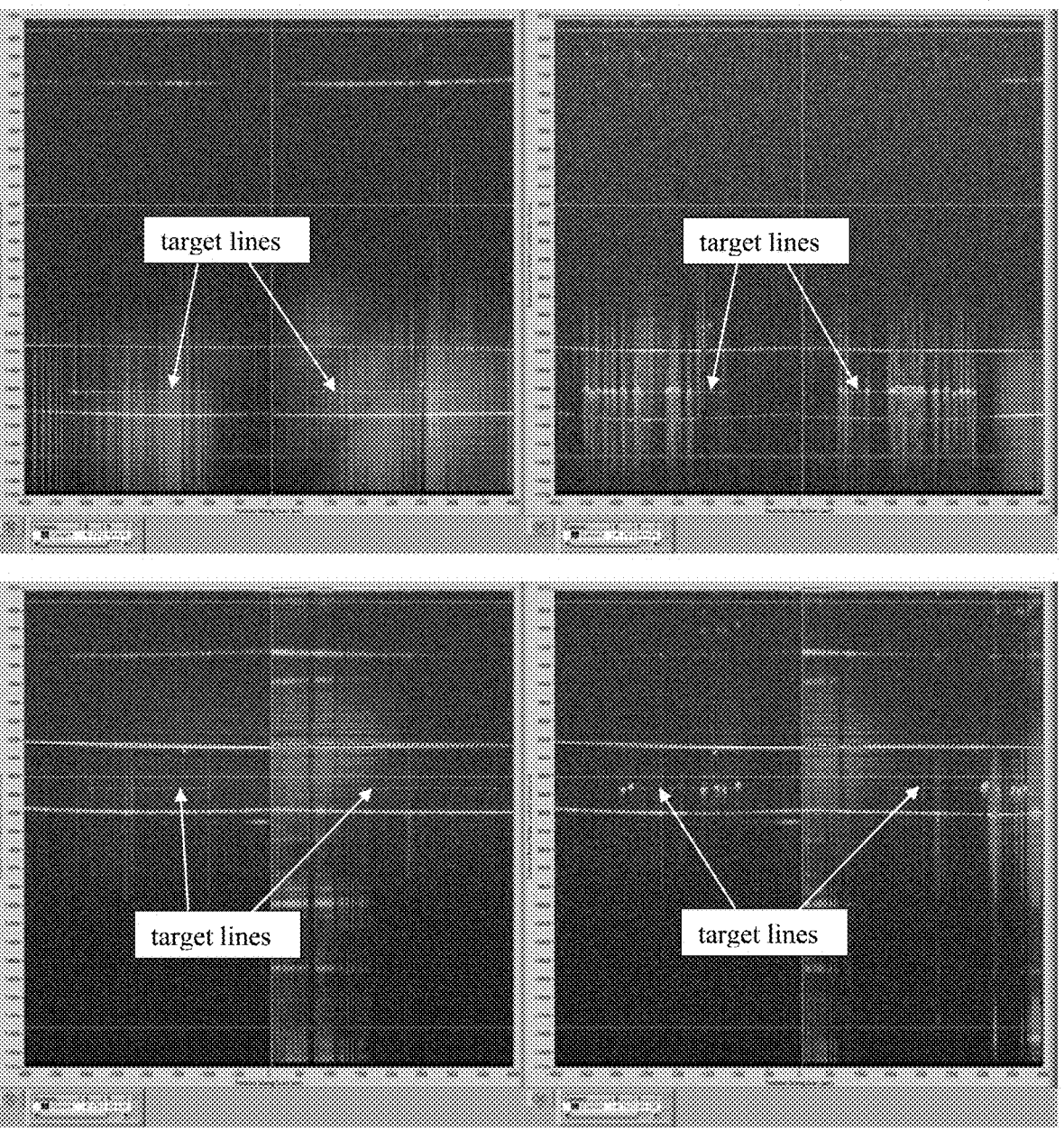
FIG. 6 shows OCT images of an IOL material button, showing damages observed in a calibration process according to an embodiment of the present invention.

FIG. 6 shows OCT images of an IOL material button, showing damage compared to the targeted line (yellow). The two upper images show the button in lower target position with higher numerical aperture. The first appearance of damage occurred at repeat #20 as seen in the upper left image. The upper right image shows the appearance of the same area after repeat #32. The two lower images show the button in higher target position with lower numerical aperture. The first appearance of damage occurred at repeat #23 as seen in the bottom left image. The lower right image shows the appearance of the same area after repeat #32.

The above-described laser system calibration method may also be used in other femtosecond laser scanning applications which require 3D targeting, such as LASIK flap cutting, lenticule extraction, corneal correction by refractive index change, as well as material machining.

It will be apparent to those skilled in the art that various modification and variations can be made in the ophthalmic laser system calibration method and related apparatus of the present invention without departing from the spirit or scope of the invention. Thus, it is intended that the present invention cover modifications and variations that come within the scope of the appended claims and their equivalents.

What is claimed is:

1. A method for calibrating and operating an ophthalmic laser system, comprising:

generating a low energy pulsed laser beam, the low energy laser beam having a pulse energy configured to cause formation of damages in an IOL (intraocular lens) material only after multiple irradiations;

controlling a laser delivery optical subsystem of the ophthalmic laser system to repeatedly scan the low energy laser beam in a piece of the IOL material;

controlling an imaging subsystem of the ophthalmic laser system to measure formation of damages in the piece of IOL material after repeats of laser scans, and to determine a rate of damage formation; and determining an effective laser intensity of the laser beam based on the rate of damage formation.

2. The method of claim 1, further comprising:

determining a laser treatment plan based on the effective laser intensity; and operating the ophthalmic laser system according to the laser treatment plan to treat a patient's eye, including generating a treatment laser beam and scanning the treatment laser beam in the patient's eye.

3. The method of claim 1, wherein the step of controlling the imaging subsystem of the ophthalmic laser system to measure the formation of damages in the piece of IOL material includes controlling a video camera or an OCT (optical coherence tomography) device of the ophthalmic laser system to measure the formation of damages in the piece of IOL material.

* * * * *